(12) United States Patent
Deshaies et al.

(10) Patent No.: US 7,041,298 B2
(45) Date of Patent: May 9, 2006

(54) PROTEOLYSIS TARGETING CHIMERIC PHARMACEUTICAL

(75) Inventors: Raymond J. Deshaies, Claremont, CA (US); Craig Crews, New Haven, CT (US); Kathleen M. Sakamoto, Manhattan Beach, CA (US)

(73) Assignees: California Institute of Technology, Pasadena, CA (US); Yale School of Medicine, New Haven, CT (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/953,473

(22) Filed: Sep. 10, 2001

(65) Prior Publication Data

US 2002/0068063 A1 Jun. 6, 2002

Related U.S. Application Data

(60) Provisional application No. 60/231,359, filed on Sep. 8, 2000.

(51) Int. Cl.
*A61K 39/385* (2006.01)
(52) U.S. Cl. .............................. 424/193.1; 424/192.1; 424/194.1
(58) Field of Classification Search .............. 424/192.1, 424/193.1, 194.1, 195.11; 435/489; 950/30; 560/300, 387.3, 323
See application file for complete search history.

(56) References Cited

U.S. PATENT DOCUMENTS 5,292,638 A * 3/1994 Benz et al. ..................... 435/6
6,306,663 B1 10/2001 Kenten et al. ............... 436/501
6,316,003 B1 11/2001 Frankel et al. .............. 424/196

FOREIGN PATENT DOCUMENTS

WO  WO 99/13077  3/1999
WO  WO 00/22110  4/2000

OTHER PUBLICATIONS

Skamoto, Kathleen M. et al., "Protacs: Chimeric Molecules that Target Proteins to the Skp1-Cullin-F Box Complex for Ubiquitination and Degradation," PNAS, vol. 98, No. 15, Jul. 17, 2001, pp. 8554-8559.

Gosink, M. and Vierstra, R., "Redirecting the specificity of ubiquitination by modifying ubiquitin-conjugating enzymes", *Proc. Natl. Acad. Sci.*, vol. 92, pp. 9117-9121, 1995.

Maniatis, Tom, "A ubiquitin ligase complex essential for the Nf-κB, Wnt/Wingless, and Hedgehog signaling pathways", *Genes & Development.*, vol. 13, pp. 505-510, 1999.

Weissman, A. "Regulating protein degradation by ubiquitination", *Immunology Today*, vol. 18, No. 4, pp. 189-198, 1997.

Yaron, A. et al., "Identification of the receptor component of the IκBα-ubiquitin ligase", *Nature*, vol. 396, No. 6711, pp. 590-594, 1998.

Yeh, Ed. et al, "Ubiquitin-like proteins: new wines in new bottles", *Gene*, vol. 248, No. 1-2, pp. 1-14, 2000.

Zhou, P. et al, "Harnessing the Ubiquitination Machinery to Target the Degradation of Specific Cellular Proteins", *Molecular Cell*, vol. 6, pp. 751-756, 2000.

Nawaz, et al., Proteasome-Dependent Degradation of the Human Estrogen Receptor, PNAS 96:1858-1862 (Mar. 1999).

Ivan, M. et al., "HIFα Targeted for VHL-Mediated Destruction by Proline Hydroxylation: Implications for $O_2$ Sensing", *Science*, vol. 292, No. 5516, pp. 464-468, 2001.

Kwon, Y.T. et al., "Bivalent Inhibitor of the N-end Rule Pathway", *J. Biol. Chem.*, vol. 274, No. 25, pp. 18135-18139, 1999.

Min, J.H. et al., "Structure of an HIF-1α-pVHL Complex: Hydroxyproline Recognition in Signaling", *Science*, vol. 296, No. 5574, pp. 1886-1889, 2002.

Zheng, N. et al, "Structure of a c-Cbl-UbcH7 Complex: RING Domain Function in Ubiquitin-Protein Ligases", *Cell*, vol. 102, No. 4, pp. 533-539, 2000.

* cited by examiner

*Primary Examiner*—Ulrike Winkler
(74) *Attorney, Agent, or Firm*—DLA Piper Rudnick Gray Cary US LLP

(57) ABSTRACT

The present invention is based on the discovery of a composition that provides targeted ubiquitination. Specifically the composition contains an ubiquitin pathway protein binding moiety which recognizes an ubiquitin pathway protein and a targeting moiety which recognizes a target protein. In addition, the present invention provides libraries of compositions, where each composition contains an ubiquitin pathway protein binding moiety and a member of a molecular library. The libraries of the present invention can be used to identify proteins involved in a predetermined function of cells.

4 Claims, 8 Drawing Sheets

PROTEOLYSIS TARGETING CHIMERIC PHARMACEUTICAL

CROSS REFERENCE TO RELATED APPLICATIONS

This application claims priority under 35 U.S.C. 119(e)(1) to U.S. Provisional Application No. 60/231,359, filed on Sep. 8, 2000, which is incorporated herein by reference.

FIELD OF THE INVENTION

This invention relates generally to the field of ubiquitin-dependent proteolysis, and more specifically to targeted ubiquitination by chimeric constructs.

BACKGROUND OF THE INVENTION

Degradation of cellular proteins is required for normal maintenance of cellular function, including proliferation, differentiation, and cell death. The irreversible nature of proteolysis makes it well-suited to serve as a regulatory switch for controlling unidirectional processes. This principle is evident in the control of the cell cycle, where initiation of DNA replication, chromosome segregation, and exit from mitosis are triggered by the destruction of key regulatory proteins.

One of the major pathways to regulate proteins posttranslationally is ubiquitin-dependent proteolysis. The first step in selective degradation is the ligation of one or more ubiquitin molecules to a protein substrate. Ubiquitination occurs through the activity of ubiquitin-activating enzymes (E1), ubiquitin-conjugating enzymes (E2), and ubiquitin-protein ligases (E3), which act sequentially to catalyze the attachment of ubiquitin to lysine residues of substrate proteins (See Ciechanover A., et al., *BioEssays,* 22:442–451 (2000)). The E3s confer specificity to ubiquitination reactions by binding directly to substrate.

There is a need in the art to provide methods and compositions useful for regulating protein activities, especially in vivo. There is also a need in the art to provide methods for identifying proteins involved in a predetermined function or phenotype.

SUMMARY OF THE INVENTION

The present invention is based on the discovery that a ubiquitin pathway protein ubiquitinates any target protein once the ubiquitin pathway protein and the target protein are placed in proximity by a chimeric construct that binds the ubiquitin pathway protein and the target protein. Accordingly the present invention provides a composition that ubiquitinates a target protein. The present invention also provides a library of compositions and the use thereof.

In one embodiment, the present invention provides a composition useful for regulating protein activity. The composition comprises a ubiquitin pathway protein binding moiety and a targeting moiety, wherein the ubiquitin pathway protein binding moiety recognizes a ubiquitin pathway protein and the targeting moiety recognizes a target protein and wherein the ubiquitin pathway protein binding moiety is coupled to the targeting moiety.

In another embodiment, the present invention provides a library. The library comprises more than one composition wherein each composition has a formula of A-B, wherein A is a ubiquitin pathway protein binding moiety and B is a member of a molecular library, wherein A is coupled to B, and wherein the ubiquitin pathway protein binding moiety recognizes an ubiquitin pathway protein.

In yet another embodiment, the present invention provides a method of ubiquitinating a target protein in a cell. The method comprises administering a composition comprising a ubiquitin pathway protein binding moiety and a targeting moiety, wherein the ubiquitin pathway protein binding moiety is coupled to the targeting moiety and wherein the ubiquitin pathway protein binding moiety recognizes an ubiquitin pathway protein and the targeting moiety recognizes the target protein.

In still another embodiment, the present invention provides a method of screening a library of the present invention to identify a composition containing a targeting moiety which recognizes a target protein associated with a predetermined function of a cell. The method comprises incubating a cell with a pool of entities from the library; monitoring the predetermined function of the cell; identifying a pool of entities that change the predetermined function of the cell; incubating the cell with a composition from the identified pool of entities; monitoring the predetermined function of the cell; and identifying a composition that changes the predetermined function of the cell, wherein the identified composition contains a targeting moiety which recognizes a target protein associated with the predetermined function.

In another embodiment, the present invention provides a method of screening a library of the present invention to identify a composition containing a targeting moiety which recognizes a target protein associated with a predetermined function of a cell. The method comprises incubating a cell with each composition from the library; monitoring the predetermined function of the cell; identifying a composition that changes the predetermined function of the cell; wherein the identified composition contains a targeting moiety which recognizes a target protein associated with the predetermined function.

In another embodiment, the present invention provides a method of identifying a target protein associated with a predetermined function of a cell. The method comprises incubating a cell with a composition from the library of the present invention; monitoring the predetermined function of the cell; identifying a composition that changes the predetermined function of the cell; identifying a target protein that binds to the identified composition, wherein the target protein is associated with the predetermined function of the cell.

In yet another embodiment, the present invention provides a method of identifying a target protein associated with a predetermined function of a cell. The method comprises incubating a cell with a pool of entities from the library of the present invention; monitoring the predetermined function of the cell; identifying a pool of entities that change the predetermined function of the cell; incubating the cell with a composition from the identified pool of entities; monitoring the predetermined function of the cell; identifying a composition that changes the predetermined function of the cell; and identifying a target protein that binds to the identified composition, wherein the target protein is associated with the predetermined function of the cell.

SUMMARY OF THE FIGURES

FIG. 1A shows that Protac-1 targets MetAP-2 to SCF. Protac-1 is a chimeric molecule that consists of a phosphopeptide moiety and a small molecule moiety that interacts with the protein target. Ub, ubiquitin; H, Hrt1. FIG. 1B shows the synthesis scheme for Protac-1. Fmoc, fluorenylmethoxy-carbonyl; DMF, dimethylformamide; DMAP, dimethylaminopyridine; DSS, disuccinimidyl suberate.

FIG. 2A shows that MetAP-2 (9 µM) was incubated with increasing concentrations of Protac-1 at room temperature for 45 min. The last two lanes depict MetAP-2 that was incubated with the individual components of protac-1: either free IPP (50 µM) or free OVA (50 µM), as indicated (IPP stands for IkB phosphopeptide, and OVA stands for ovalicin). After incubation, samples were supplemented with SDS/PAGE loading buffer, separated by SDS/PAGE, and immunoblotted with MetAP-2 antiserum. FIG. 2B shows the same as 2A, except MetAP-2 (9 µM) plus Protac-1 (10 µM) were supplemented with either IPP (50 µM) or OVA (50 µM), as indicated. Protac binding to MetAP-2 was inhibited by the addition of OVA, but not by the addition of IPP.

FIG. 4A shows ubiquitination of the 46-kDa fragment of MetAP-2. MetAP-2-Protac-1 mixture was added to either control (Mock) or $SCF^{\beta-TRCP}$ beads (1) supplemented with ATP plus purified E1, E2 (Cdc34), and ubiquitin. The E2, UbcH5c (500 ng), was also tested in the reaction, which resulted in the same degree of ubiquitination as observed with Cdc34 (data not shown). Reactions were incubated for 1 hr at 30° C. and were evaluated by SDS/PAGE followed by Western blotting with anti-MetAP-2 antiserum. FIG. 4B shows ubiquitination of full-length (67-kDa) MetAP-2. Same as FIG. 4A, except that the 67-kDa preparation of MetAP-2 was used, and E1, E2, plus ubiquitin were either added at normal (1×) or 2-fold higher (2×) levels, as indicated. FIG. 4C shows that ubiquitination of MetAP-2 by $SCF^{\beta-TRCP}$ depends on Protac-1. Same as A, except that methylubiquitin (Me) was substituted for ubiquitin, as indicated, and the reactions depicted in lanes 5–7 lacked Protac-1. In lane 7, unlinked IPP and OVA were added at 100 µM in place of Protac-1. FIG. 4D shows that Protac-1-dependent ubiquitination of MetAP-2 is competitively inhibited by IPP. Same as FIG. 4A, except that reactions in lanes 3 and 4 were supplemented with 100 µM each IPP and OVA, respectively.

DESCRIPTION OF THE PREFERRED EMBODIMENTS

Figure 1A:
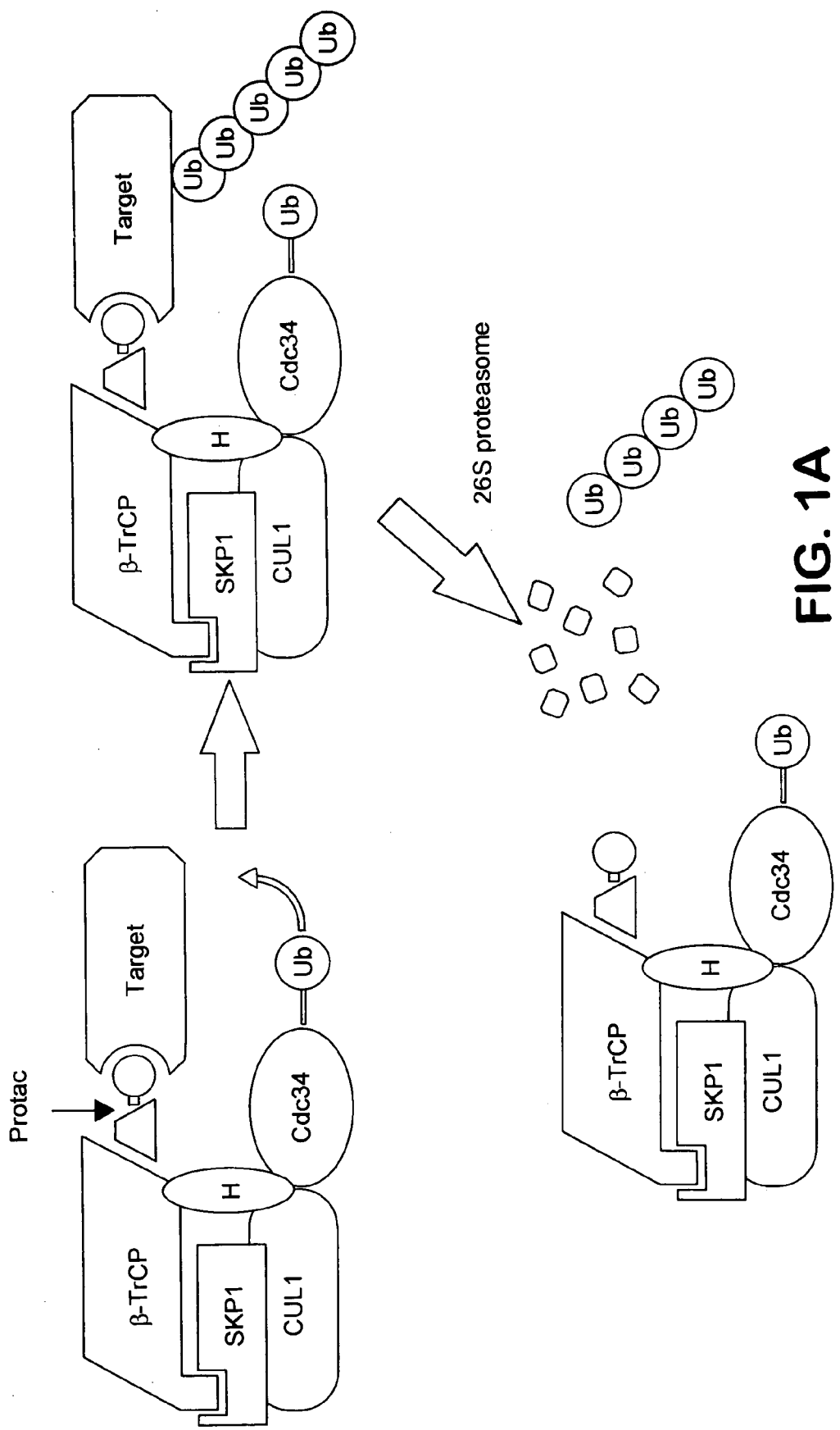
FIG. 1A and 1B show a schematic representation of a general scheme for Protac-1.

The present invention relates in general to targeted ubiquitination using a composition, e.g., a chimeric construct containing a ubiquitin pathway protein binding moiety and a targeting moiety. The present invention also provides a library of compositions useful for identifying proteins associated or involved with a predetermined function of cells.

According to the present invention, a ubiquitin pathway protein binding moiety is any suitable structure that recognizes and binds to a ubiquitin pathway protein. In general, a ubiquitin pathway protein is any entity or complex that is capable of catalyzing or causing to catalyze the transfer of a ubiquitin or ubiquitin-like modifying polypeptide, e.g., Nedd8, APG12 or ISG15/UCRP to another protein. In one embodiment, an ubiquitin pathway protein is a ubiquitin protein ligase or E3 protein. There are at least 100 distinct E3 proteins encoded by the human genome (See Winston, J., et al., Curr. Bio., 9:1180–82 (1999)). For example, one particular class of E3 proteins are Skp1-Cullin-F box (SCF) complexes, each complex containing Skp1, a member of Cullin family, e.g., the RING-H2 protein Hrt1, also known as Roc1 or Rbx1, and an F box protein (See Deshaies, R. J., Annu. Rev. Cell Dev. Biol., 15:435–67 (1999)). These components are conserved from yeast to mammals.

In another embodiment, an ubiquitin pathway protein is a protein that is involved in or a component of a ubiquitin-like pathway, which transfers ubiquitin-like modifying polypeptides, e.g., SUMO, Nedd8, APG12 or ISG15/UCRP. Components of a ubiquitin-like pathway are usually homologues of a ubiquitin pathway. For example, the ubiquitin-like pathway for SUMO includes a homologue of a ubiquitin protein activating enzyme or E1 protein, ubiquitin protein conjugating enzyme or E2 protein and ubiquitin ligase or E3 protein.

A ubiquitin pathway protein can be expressed in a tissue specific or regulated manner. For example, VACM-1 receptor (aka CUL-5), and F-box protein, NFB42 are expressed in a tissue specific manner. In one embodiment, an ubiquitin pathway protein is an RING-based or HECT-based ubiquitin ligase.

According to one embodiment of the present invention, an ubiquitin pathway protein binding moiety of the present invention is any suitable ligand to an ubiquitin pathway protein, e.g., ubiquitin protein ligase or E3 protein or homologues thereof. In another embodiment, an ubiquitin pathway protein binding moiety of the present invention is any ubiquitin pathway protein binding peptide, domain or region of an ligand to an ubiquitin pathway protein. In still another embodiment, an ubiquitin pathway protein binding moiety of the present invention recognizes and binds to an ubiquitin pathway protein in a regulated manner. For example, IkBalpha is a well defined ligand for mammalian $SCF^{\beta-TRCP}$ complex. The mammalian F box protein, β-TRCP/E3RS, has been shown to bind IkBalpha, a negative regulator of NFkB (See Yaron, A., et al., Nature (London), 396:590–94 (1998)). The $SCF^{\beta-TRCP}$ complex promotes the ubiquitination and subsequent degradation of IkBalpha, which results in activation of NFkB during the inflammatory response (See Deshaies, R. J., Annu. Rev. Cell Dev. Biol., 15:435–67 (1999)). The recruitment of IkBalpha to $SCF^{\beta-TRCP}$ is mediated by a ubiquitin pathway protein binding domain, which is a 10-aa peptide within IkBalpha, DRHDSGLDSM (SEQ ID NO:1) (See Yaron, A., et al., *Nature (London)*, 396: 590–94 (1998); and Yaron, A., et al., *EMBO J.*, 16: 6486–94 (1997)). In response to diverse inflammatory signals, IkBa kinase (IKK) phosphorylates this motif on both serines, which triggers the binding of IkBalpha to β-TRCP.

According to the present invention, a targeting moiety is any structure that recognizes and binds to a target protein. A target protein can be any protein that one desires to regulate its level or activity, e.g., to alter the activity through ubiquitin-dependent proteolysis or through attachment of ubiquitin or ubiquitin-like modifying polypeptide to lysine residues that are important for the protein's activity or structure. For example, a target protein can be a protein involved in cell cycle, signal transduction, cell differentiation, cell dedifferentiation, cell growth, production of cytokines or other biological modifiers, production of regulatory or functional proteins, pro-inflammatory signaling, or the glucose regulation pathway. In one embodiment, a target protein can be a protein that is not known to be ubiquitinated or not known to be a substrate for any ubiquitin pathway protein.

In another embodiment, a target protein is a disease related protein, e.g., a protein for which changes in its function or activity cause disease, or whose function is considered important to the propagation of the disease state. The target protein may be either stable or unstable, e.g., androgen receptor, estrogen receptor, myc, cyclin B, Ras, or cyclin E.

In still another embodiment, a target protein is methionine aminopeptidase-2 (MetAP-2). MetAP-2 catalyzes the cleavage of N-terminal methionine from nascent polypeptides (See Li, X., et al. *Proc. Natl. Acad. Sci. USA*, 92:12357–61 (1995)) and is the primary target of the potent angiogenesis inhibitors fumagillin and ovalicin (OVA; See Sin, N., et al., *Proc. Natl. Acad. Sci. USA*, 94:6099–103 (1997); and Griffith, E., et al., *Chem. Biol.*, 4:461–71 (1997)). Both of these compounds inhibit MetAP-2 by covalently binding His-231 in the active site. The consequent reduction in MetAP-2 activity blocks endothelial cell proliferation by causing p53-dependent arrest in the G1 phase of the cell cycle (See Yeh, J., et al., *Proc. Natl. Acad. Sci. USA*, 97: 12782–87 (2000)).

Structures that recognize and bind to a target protein are well known or readily available to one skilled in the art. For example, a targeting moiety for MetAP-2 can be an angiogenesis inhibitor including, without limitation, fumagillin and ovalicin. In one embodiment, a targeting moiety can be the binding domain of a polypeptide or protein that recognizes and binds to a desired protein, e.g., target protein.

According to the present invention, the composition of the present invention may further comprise a cell delivering moiety. A cell delivering moiety is any structure that facilitates the delivery of the composition or promotes transduction of the composition into cells. In one embodiment, a cell delivering moiety is derived from virus protein or peptide, e.g., a tat peptide. In another embodiment, a cell delivering moiety is a hydrophobic compound capable of penetrating cell membranes. Alternatively, a ubiquitin pathway protein binding moiety that is more susceptible for cell membrane penetration is used to enhance the cell membrane transduction of the composition. For example, an ubiquitin pathway protein binding peptide derived from the HIV Vpu protein.

According to the present invention, the ubiquitin pathway protein binding moiety can be coupled, e.g., covalently by any suitable means to the targeting moiety. For example, an ubiquitin pathway protein binding moiety, IkBalpha peptide is coupled to a targeting moiety, OVA through Fmoc-Gly. In one embodiment, the composition of the present invention is a chimeric fusion protein and is encoded by a polynucleotide in an expression system. In another embodiment, the ubiquitin pathway protein binding moiety is covalently coupled to the targeting moiety through a linker, e.g., a linker which has a binding domain for the ubiquitin pathway protein binding moiety as well as targeting moiety.

In yet another embodiment, the ubiquitin pathway protein binding moiety can be coupled noncovalently to the targeting moiety upon the presence of a signal factor, e.g., the presence or the level of an intracellular metabolite, regulatory protein, etc. For example, the ubiquitin pathway protein binding moiety and the targeting moiety can be coupled when they simultaneously chelate an intracellular metabolite.

In still another embodiment, the ubiquitin pathway protein binding moiety can include a first coupling moiety and the targeting moiety can include a second coupling moiety such that the first and the second coupling moiety are coupled or bind to each other in the presence of a signal factor or enzymatic activity in vitro or in vivo (e.g., phosphorylation of the first coupling moiety by a kinase that is produced by cancer cells enables it to bind to the second coupling moiety.

Another feature of the present invention provides a library of the compositions of the present invention. In one embodiment, the targeting moiety of the composition of the library is a member of a molecular library. A molecular library can be any collection of molecules, including without limitation, a combinatorial library, a small molecule library, a receptor library, and a ligand library. In one embodiment, a member of a molecular library is covalently coupled to the ubiquitin pathway protein binding moiety, e.g., through a linker.

The compositions and the libraries of compositions provided by the present invention can be used individually or collectively as a group to perform target ubiquintination. Such target ubiquitination is useful for regulating protein levels or activities, thus providing therapeutic treatment for disease conditions. One or more compositions of the present invention can be administered to ubiquitinate a target protein either in vitro or in vivo. In one embodiment, two or more compositions of the present invention with the same targeting moiety, but different ubiquitin pathway protein binding moieties are administered to cells to ubiquitinate a target protein, e.g., ubiquitinate a target protein with a desired rate or degree. In another embodiment two or more compositions of the present invention with the same ubiquitin pathway protein binding moiety, but different targeting moiety are administered to cells to ubiquitinate different target proteins. In still another embodiment, one or more compositions with a ubiquitin pathway protein binding moiety that recognizes a ubiquitin pathway protein expressed in a tissue specific manner are administered to cells to ubiquitinate one or more target proteins in a tissue specific manner, e.g., at a specific location.

The compositions of the present invention useful for therapeutic treatment can be administered alone, in a composition with a suitable pharmaceutical carrier, or in combination with other therapeutic agents. An effective amount of the compositions to be administered can be determined on a case-by-case basis. Factors should be considered usually include age, body weight, stage of the condition, other disease conditions, duration of the treatment, and the response to the initial treatment.

Typically, the compositions are prepared as an injectable, either as a liquid solution or suspension. However, solid forms suitable for solution in, or suspension in, liquid vehicles prior to injection can also be prepared. The composition can also be formulated into an enteric-coated tablet or gel capsule according to known methods in the art.

The compositions of the present invention may be administered in any way which is medically acceptable which may depend on the disease condition or injury being treated. Possible administration routes include injections, by parenteral routes such as intravascular, intravenous, intraepidural or others, as well as oral, nasal, ophthalmic, rectal, topical, or pulmonary, e.g., by inhalation. The compositions may also be directly applied to tissue surfaces, e.g., during surgery. Sustained release administration is also specifically included in the invention, by such means as depot injections or erodible implants.

According to another feature of the present invention, the libraries of compositions provided by the present invention are useful for identifying target proteins that are involved in a predetermined function. For example, compositions of the libraries of the present invention can be screened either individually or be divided into a first subset of different pools of compositions for screening. Cells are incubated with and without each composition or pool of compositions and a predetermined function of the cells is monitored to determine the effect of each composition or pool of compositions.

A predetermined function of cells can be any relevant or interested function, including without limitation, cell growth, cell death, cell cycle regulation, cell differentiation, cell dedifferentiation, pro-inflammatory signaling, signal transduction, cytokine production, production of regulatory or functional proteins, and glucose regulation.

If a pool of compositions is identified as affecting a predetermined function of cells, then the identified pool of compositions is broken down further into a second subset of pools to repeat the same type of screening with the first subset of pools. Such subdivision of pools can be repeated as many times as necessary so that at the end the identified pool has a reasonable number of compositions to be screened individually.

An individual composition identified as affecting a predetermined function of cells contains a targeting moiety that recognizes a target protein involved in the predetermined function of cells. Such identified composition can be used either therapeutically to affect the predetermined function of cells or to screen cell extracts or expression libraries to identify proteins that bind to the targeting moiety of the identified composition, e.g., target proteins, thus identify proteins involved in the predetermined function of cells. The identified target proteins are useful for developing novel drugs or therapeutic treatments.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Synthesis of I kBa-OVA Protac.

OVA(1.4 mmol) was dissolved in 10 ml of methanol at 0° C., and NaBH4 (3.0 mmol) was added slowly. After 30 min of stirring, methanol was removed under reduced pressure, and the resulting crude product was purified by flash column chromatography to yield ovalicinol (1.15 mmol, 82%).

Fmoc-Gly was coupled to the ovalicinol to give Fmoc-Gly-ovalicinol. Specifically, dimethylformamide (DMF, 28 μl) was added to dichloromethane solution (30 ml) containing Fmoc-Gly-OH (3.56 mmol) and oxalyl chloride (7.12 mmol) at 0° C. After 3 hr of stirring at room temperature, dichloromethane was removed under nitrogen atmosphere. The resulting solid residue was redissolved in dichloromethane (10 ml) and was combined with ovalicinol (0.6 mmol) and dimethylaminopyridine (4.7 mmol) in dichloromethane (30 ml) at 0° C. The reaction mixture was stirred for 2 hr at room temperature. After dichloromethane was removed under reduced pressure, the resulting residue was flash-chromato-graphed to provide Fmoc-Gly-ovalicinol (0.39 mmol, 65%). Next, Fmoc-Gly-ovalicinol (0.09 mmol) was treated with 20% piperidine in DMF (2 ml) at room temperature for 10 min, and the DMF was removed under high vacuum. The resulting solid was redissolved in 2 ml of DMSO, and disuccin-imidyl suberate (0.9 mmol) was added at room temperature. After overnight stirring, DMSO was removed under high vacuum, and the resulting crude product was flash-chromato-graphed to give monosuccinimidyl suberate-Gly-ovalicinol (0.06 mmol, 68%).

Monosuccinimidyl suberate-Gly-ovalicinol (12 μmol) in DMSO (0.6 ml) was added to DMSO solution (1 ml) containing IkBalpha peptide (3.67 μmol) and dimethylaminopyridine (11 μmol). After 20 min stirring at room temperature, the coupling reaction was completed, which was confirmed by a Kaiser test. DMSO was removed under high vacuum, and the resulting crude product was repeatedly washed with dichloromethane and methanol to remove excess monosuccinimidyl suberate-Gly-ovalicinol to give the final product, IkBa peptide-suberate-Gly-ovalicinol (5.8 mg, 2.59 μmol, 70%). The final product was characterized by electrospray (ES) mass spectrometry. ES-MS (M 1 H) 1 for ovalicinol-Gly-suberate-IkBa peptideydimethylaminopyridine was 2,231.56 Da. All other intermediates were characterized by 500-MHz $^1$H NMR spectroscopy.

MetAP-2-Protac-1 Coupling Assay.

MetAP-2 (9 μM) was incubated with increasing concentrations of Protac-1 (dissolved in water) at room temperature for 45 min. Reactions were supplemented with SDS loading dye, fractionated on an SDS/10% polyacryl-amide gel, transferred onto a nitrocellulose membrane, and immunoblotted with rabbit polyclonal anti-MetAP-2 antiserum (Zymed). Enhanced chemiluminescence was performed by using Amersham Pharmacia detection reagents.

Tissue Culture and Transfections.

293T cells were cultured in DMEM with 10% (vol/vol) FBS (GIBCO), penicillin (100 units/ml), strep-tomycin (100 mg/ml), and L-glutamine (2 mM). Cells were split 1:5 before the day of transfection and transiently transfected with 40 μg of plasmid. Cells were 60% confluent in 100-mm dishes on the day of transfection. DNA [20 μg of pFLAG-Cul1(RDB1347) and 20 μg of pFLAG-β-TRCP(RDB1189)] was added and the cells were transfected using calcium phosphate precipitation, as described (See Lyapina, S. A., et al., *Proc. Natl. Acad. Sci. USA*, 95:7451–56 (1998)). Cells were harvested 30 hr after transfection. Five micrograms of pGL-1, a plasmid containing the cytomegalovirus (CMV) promoter linked to the green fluorescent protein (GFP) cDNA, was cotransfected into cells at the same time to assess transfection efficiency. In all experiments, greater than 80% of the cells were GFP-positive at the time of harvesting.

Immunoprecipitation and Ubiquitination Assays.

293T cell pellets were lysed with 200 μl of lysis buffer (25 mMTriszCl, pH 7.5y150 mM NaCly0.1% Triton X-100y5 mM NaFy0.05 mM EGTAy1 mM PMSF). Pellets from cells transfected with vector, pFLAG-β-TRCP, or pFLAG-Cul-1 were vortexed for 10 sec, then incubated on ice for 15 min. After centrifugation at 13,000 rpm in an Eppendorf microfuge (Germany) for 5 min at 4° C., the supernatant was added to 20 μl of FLAG M2 beads (Sigma), which were washed with lysis buffer three times before immu-noprecipitation. Lysates were incubated with the beads on a rotator for 2 hr at 4° C., followed by one wash with buffer A (25 mM Hepes buffer, pH 7.4y0.01% Triton X-100y150 mM NaCl) and one wash with buffer B (the same buffer without the Triton X-100). For binding assays (FIG. 3), 50% (10 μl) of the 9 μM MetAP-2/50 μM Protac-1 mixture was loaded as input; the other 50% was added to the beads. After the addition of ligand, the beads were rotated at room temperature for 1 hr. The beads were washed once each with buffers A and B. After centrifugation at 13,000 rpm in an Eppendorf microfuge (Germany) for 1 min, half of the bead and supernatant fractions, representing bound and unbound, respectively, were evaluated by Western blotting as described above. For ubiquitination reactions, 4 μl of 18 μM MetAP-2, 4 μl of 100 μM Protac-1, 0.5 ml of 0.1 μl purified mouse E1, 1 μl of 0.5 μg/μl human Cdc34 E2, and 1 μl of 25 mM ATP were added to 20 μl (packed volume) of washed FLAG-M2 beads. For competition experiments, the IPP (100 μM final) or OVA(100 μM final) was added simultaneously with the Protac-1. Reactions were incubated for 1 hr at 30° C. in a thermomixer (Eppendorf) with constant mixing. SDS/PAGE loading buffer was added to terminate reactions, which were evaluated by Western blotting as described above.

The experiments performed herein used two different preparations of MetAP-2. One preparation consisted primarily of a 47-kDa fragment that was generated either by a contaminating protease or by slow autoproteolysis. The second preparation consisted almost entirely of full-length 67-kDa MetAP-2. Essentially identical results were obtained with both preparations.

Degradation Experiments with *Xenopus* Extracts.

Extracts from unfertilized *Xenopus laevis* eggs were prepared the day of the experiment, as described (See Murray, A. W., *Methods Cell Biol.*, 3:581–605 (1991)). The MetAP-2-Protac-1 mixture (4 μl of 9 μM MetAP-2 plus 50 μMProtac-1) or MetAP-2 alone was added to 10 ml of extract in addition to OVA (10 μM final), constitutively active IKK (IKK-EE, 0.4 μg), and okadaic acid (OA; 10 μM final). N-acetyl-leu-leu-norleucinal (LLnL, 50 μM final), epoxomicin (10 μM final), or DMSO vehicle were added to the indicated concentrations to inhibit degradation by the proteasome. The protease inhibitors chymostatin, pepstatin, and leupeptin (15 μg/μl final concentration) also were added to the extracts. Reactions were incubated for the indicated times at room temperature and terminated by adding 50 μl of SDS/PAGE loading buffer. Samples were evaluated by Western blotting as described above.

MetAP-2 Specifically Binds Protac-1 in Vitro.

Figure 1B:
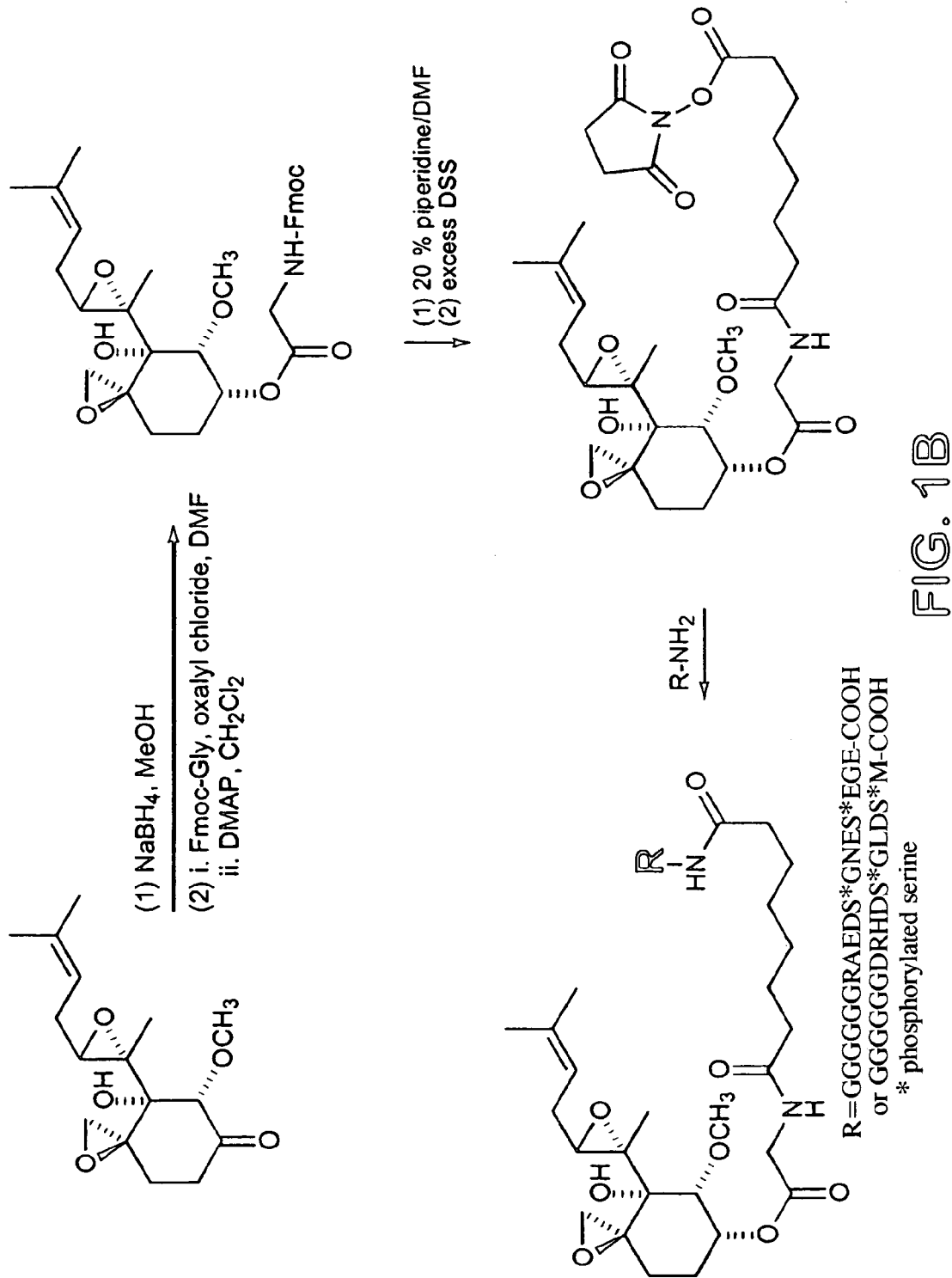
Figure 2B:
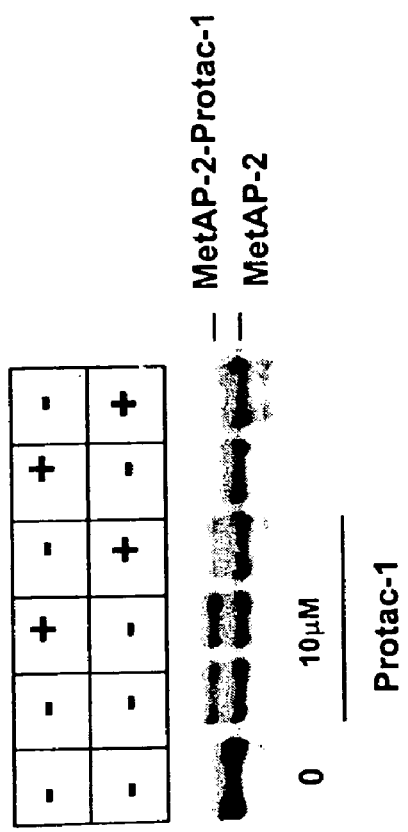
FIG. 2A and 2B shows that MetAP-2 binds Protac specifically and in a concentration-dependent manner.
Figure 2A:
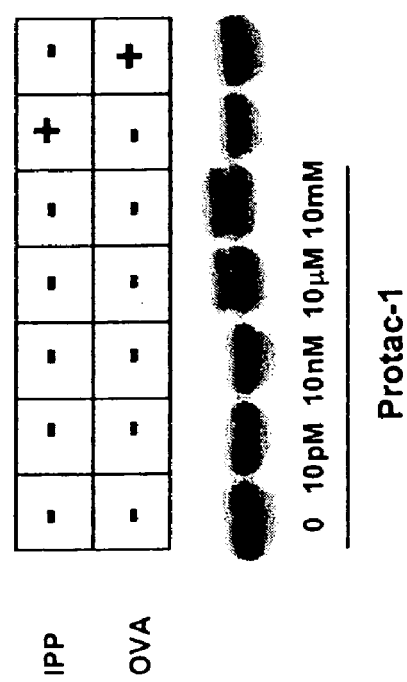

The IkBalpha-OVA chimera, Protac-1 (FIG. 1B), was synthesized as described above. To demonstrate that purified MetAP-2 bound Protac-1, we incubated MetAP-2 (18 mM) with increasing concentrations of Protac-1 (FIG. 2A). A Western blot analysis was performed with anti-MetAP-2 antiserum. At Protac-1 concentrations of 10 μM and 10 mM, two bands were observed; the lower band represents unbound MetAP-2, and the upper band represents a complex of MetAP-2 bound to Protac-1. The addition of Protac-1 at higher concentrations did not increase the yield of MetAP-2-Protac-1 complexes, suggesting that only a fraction of the MetAP-2 molecules were active and able to bind Protac-1. Combining MetAP-2 with either free IPP or free OVA did not yield the doublet observed with Protac-1. The specificity of MetAP-2 interaction with Protac-1 in vitro was also tested. Free OVA, but not free IPP, inhibited the formation of the MetAP-2-Protac-1 complex (FIG. 2B). Therefore, the results demonstrate that MetAP-2 was specifically conjugated to the OVA moiety of Protac-1 in a concentration-dependent manner.

Protac-1 Recruits MetAP-2 to SCF.

Figure 3:
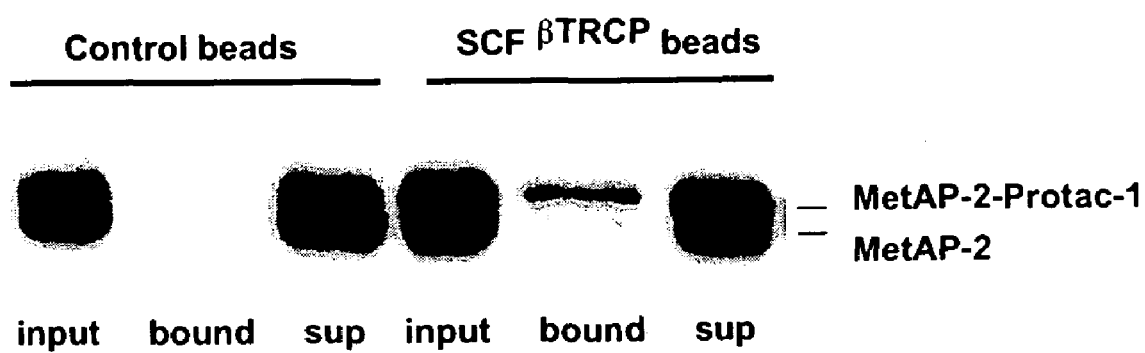
FIG. 3 shows that Protac-1 recruits MetAP-2 to $SCF^{\beta-TRCP}$. Extracts from 293T cells transiently transfected with either control vector or plasmids expressing FLAG epitope-tagged Cul-1 and β-TRCP were subject to affinity purification on anti-FLAG resin to yield either control beads or $SCF^{\beta-TRCP}$ beads. The matrices then were mixed with the preformed MetAP-2-Protac-1 complex (input), incubated, and separated into pellet (bound) and unbound (sup) fractions. Proteins were fractionated on an SDS/10% polyacrylamide gel, and immuno-blotted with anti-MetAP-2 antiserum. MetAP-2 and MetAP-2-Protac-1 refer to free MetAP-2 and MetAP-2 complexed with Protac-1, respectively.

Before testing the activity of Protac-1, an approach to isolate and assay $SCF^{\beta-TRCP}$ complexes in vitro as described (See Tan, P., et al., *Mol. Cell,* 3:327–33 (1999)) was first adapted. Lysates from 293T cells transfected with plasmids that encoded β-TRCP and Cul-1 proteins tagged with the FLAG epitope at the N terminus were immunoprecipitated with anti-FLAG antibody-conjugated resin. Immunoblot analysis confirmed that all components of $SCF^{\beta-TRCP}$ were present in the anti-FLAG immunoprecipitate, including Skp1, Hrt1, and the transfected FLAG Cul-1 and FLAG β-TRCP (data not shown). Furthermore, control experiments confirmed that these immunoprecipitates promoted ubiquitination of IKK-phosphorylated glutathione S-transferase-IkBalpha in a manner that was inhibited by the IPP and Protac-1 (data not shown; ref 7). To determine whether Protac-1 could recruit MetAP-2 to $SCF^{\beta-TRCP}$, MetAP-2 (18 μM) was first incubated with Protac-1 (100 μM) for 45 min at room temperature. After isolation of $SCF^{\beta-TRCP}$ complexes, the anti-FLAG beads were supplemented with the MetAP-2-Protac-1 mixture and rotated at room temperature for 1 hr. The beads and supernatant then were evaluated by Western blot analysis for the presence of MetAP-2. Anti-FLAG beads coated with $SCF^{\beta-TRCP}$, but not control beads preincubated with untransfected 293T cell lysates, specifically retained a fraction of the MetAP-2-Protac-1 complex and not the unliganded MetAP-2 (FIG. 3). These results demonstrate that Protac-1 specifically recruited MetAP-2 to $SCF^{\beta-TRCP}$.

Protac-1 Mediates the Ubiquitination of MetAP-2.

Figures 4A, 4B:
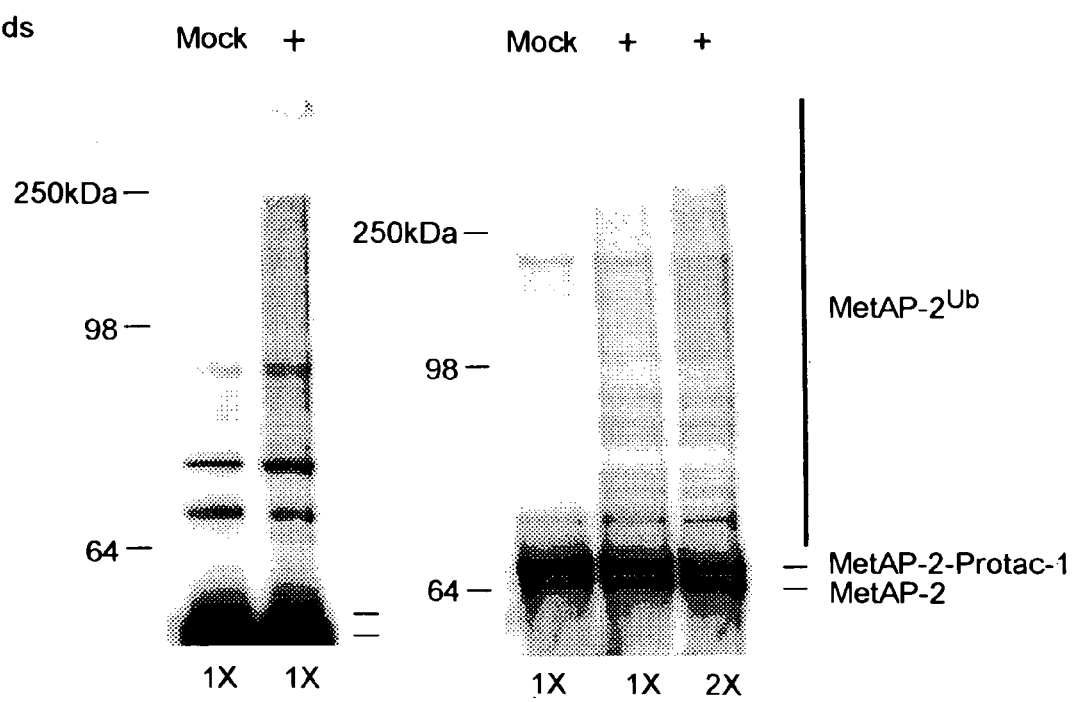
FIG. 4A, 4B, 4C, and 4D show that Protac mediates MetAP-2 ubiquitination by SCF.
Figure 4C:
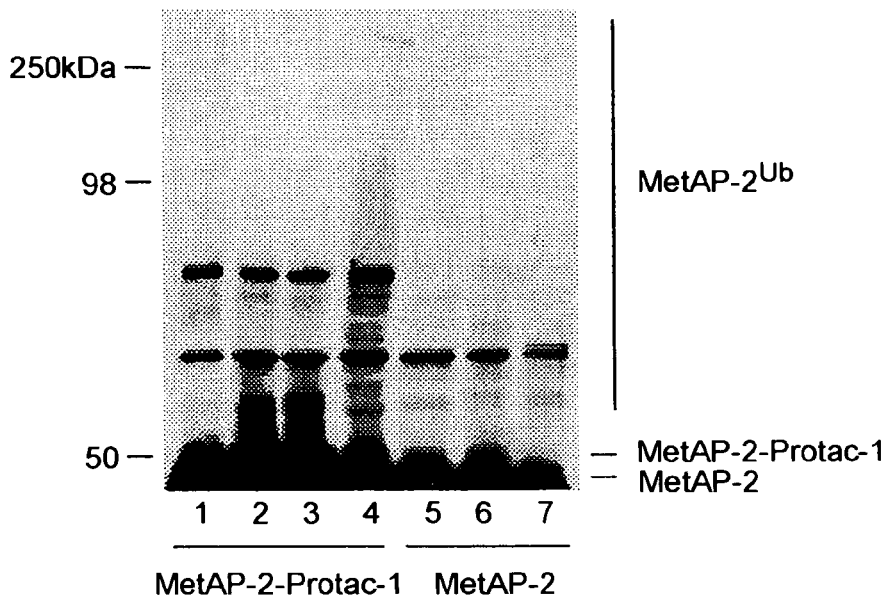
Figure 4D:
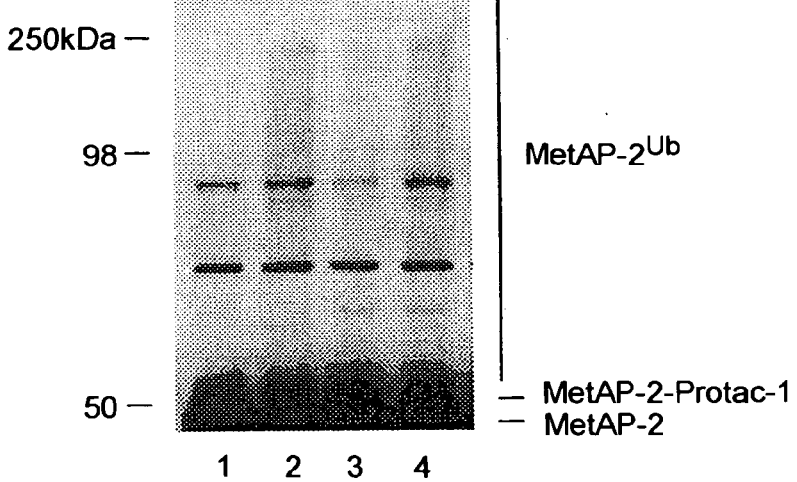

Because Protac-1 was able to tether MetAP-2 to $SCF^{\beta-TRCP}$, the question became whether MetAP-2 could be ubiquitinated. To answer this question, anti-FLAG beads coated with $SCF^{\beta-TRCP}$ was supplemented with ATP, MetAP-2-Protac-1, plus purified E1, E2 (human Cdc34), and ubiquitin. After incubation, Western blot analysis was performed with anti-MetAP-2 antiserum. This experiment was repeated with two different preparations of purified MetAP-2: one contained primarily a 47-kDa autocatalyzed cleavage product (FIG. 4A), and the other contained full-length 67-kDa protein (FIG. 4B). In both cases, MetAP-2-Protac-1 was extensively modified in the presence of $SCF^{\beta-TRCP}$-coated beads but not control beads (Mock). Substitution of the methyl ubiquitin, which acts as a chain-terminator of polyubiquitination, collapsed the high molecular weight forms of modified MetAP-2 to a series of 2–3 bands migrating directly above unmodified MetAP-2-Protac-1 complex (FIG. 4C, compare lanes 2 and 3 with lane 4), confirming that MetAP-2 was ubiquitinated by $SCF^{\beta-TRCP}$. The next test was whether MetAP-2 ubiquitination depended on Protac-1. As shown in FIG. 4C, MetAP-2 was not ubiquitinated in the absence of either $SCF^{\beta-TRCP}$ (lane 1) or Protac-1 (lanes 5 or 6; for some experiments, methyl ubiquitin was used in place of ubiquitin to simplify detection of ubiquitin conjugates). Moreover, unlinked OVA (50 mM) plus IPP (50 mM) were not able to substitute for the OVA-IPP conjugate (lane 7). Protac-1-dependent ubiquitination of MetAP-2 was specific; it was readily competed for by free IPP (FIG. 4D, lane 3 vs. lane 2). In contrast, free OVA did not compete (FIG. 4D, lane 4), presumably because it was unable to displace the Protac-1 that previously was linked covalently to MetAP-2. Taken together, these observations indicate that Protac-1 specifically elicited ubiquitination of MetAP-2 by SCF$^{\beta\text{-}TRCP}$, and that successful targeting required that the two components of Protac-1 be bound together as a chimeric molecule.

MetAP-2-Protac-1 is Degraded in *Xenopus* Egg Extracts.

Figure 5:
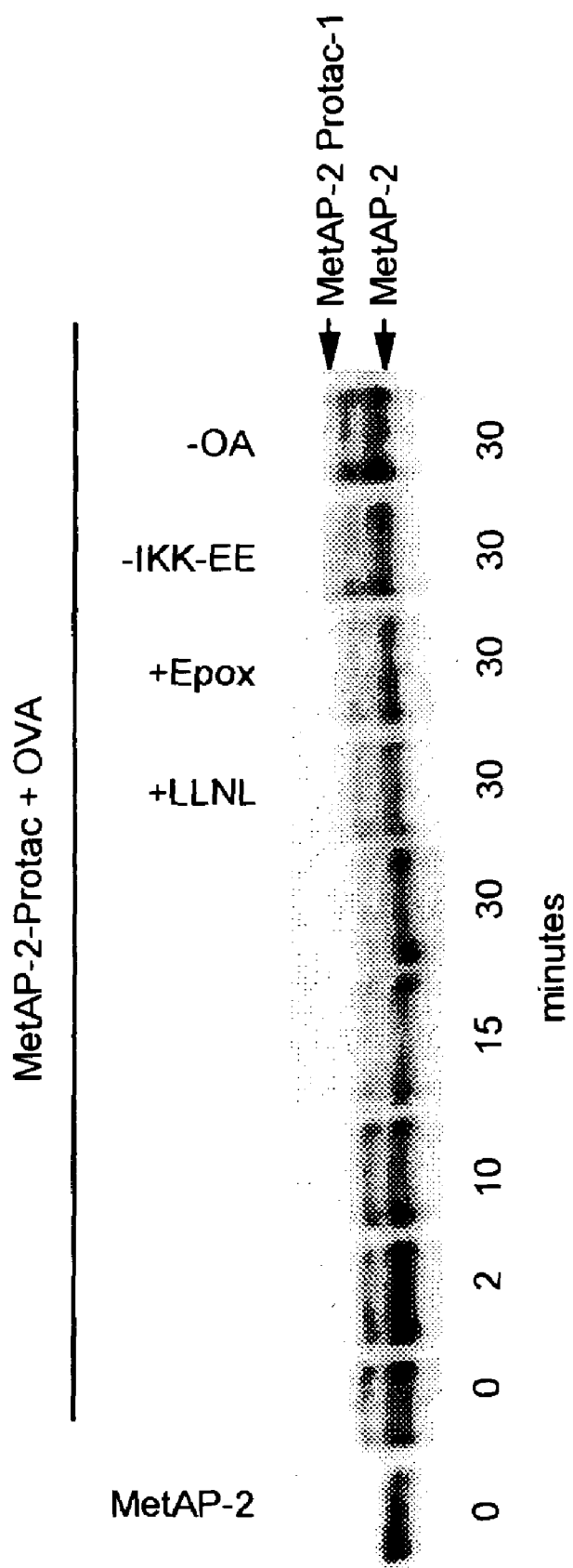
FIG. 5 shows that MetAP-2-Protac is degraded in *Xenopus* extracts. The MetAP-2-Protac-1 mixture or MetAP-2 alone was added to *Xenopus* egg extract fortified with OVA (100 µM), IKK-EE (0.4 µg), and OA (10 µM). Where indicated, reactions were either deprived of IKK-EE or OA, or were further supplemented with 50 µM LLnL or 10 µM epoxomicin (Epox). Reactions were incubated for the indicated times at room temperature, terminated by adding SDS/PAGE loading buffer, and evaluated by SDS/PAGE followed by Western blotting with anti-MetAP-2 antiserum.

The experiments described above demonstrated that MetAP-2 was ubiquitinated in a Protac-1-dependent manner by highly purified SCF$^{\beta\text{-}TRCP}$. However, the key issues are whether Protac-1 can specifically activate MetAP-2 degradation, and whether targeted degradation can be achieved by endogenous ubiquitin/proteasome pathway components at typical intracellular concentrations. To address these questions, MetAP-2 was preincubated with Protac-1 to allow the complexes to form, and then added the mixture to *Xenopus* egg extract supplemented with IKK-EE (See Mercurio, F., Zhu, et al., *Science*, 278:860–66. (1997)), OA, and OVA. The addition of IKK-EE and OA was intended to sustain phosphorylation of the IkBa peptide moiety of Protac-1, whereas OVA was added to prevent the further linkage of Protac-1 to MetAP-2. Remarkably, MetAP-2-Protac-1 complex (top band) but not MetAP-2 alone (bottom band) was mostly degraded after 30 min (FIG. 5). Degradation of MetAP-2-Protac-1 was attenuated in extracts supplemented with the proteasome inhibitors LLnL or epoxomicin (See Meng, L., et al., *Proc. Natl. Acad. Sci. USA*, 96:10403–08 (1999)), but not by other protease inhibitors (chymotrypsin, pepstatin, and leu-peptin) added to the reaction. Moreover, addition of both IKK-EE and OA was required for optimal degradation of MetAP-2-Protac-1. Similarly, we have seen specific turnover of the MetAP-2-Protac-1 complex, but not free MetAP-2, in three independent experiments. Because the IPP does not have lysines and the OVA does not have free amino groups, it is unlikely that Protac itself serves as a target for ubiquitin-dependent proteolysis. Taken together, these results demonstrate that Protac-1 targeted MetAP-2 for degradation by means of the proteasome. MetAP-2 turnover was very specific, in that maximal degradation required agents predicted to sustain phosphorylation of the IkBa peptide.

The present invention provides a method to target proteins, at will, to the ubiquitin/proteasome pathway. The linchpin of the strategy described here is the development of chimeric molecules—referred to as Protacs—that link a desired target protein to a ubiquitin ligase. A related method for inducing selective heterodimerization of proteins to regulate activation and termination of signaling pathways has been described (See Belshaw, P. J., et al., Proc. Natl. Acad. Sci. USA, 93:4604–07 (1996)).

As a target protein for a proof of principle experiment, MetAP-2, which covalently binds the angiogenesis inhibitor OVA was chosen. For the ubiquitin ligase, the SCF$^{\beta\text{-}TRCP}$ complex was chosen, for reasons described in more detail below. Although MetAP-2 has 36 lysines, it has not been reported to be an unstable protein in vivo, and it was not clear whether it would serve as a substrate for SCF$^{\beta\text{-}TRCP}$, or whether it would be degraded by the ubiquitin/proteasome pathway (See Liu, S., et al., *Science*, 282:324–27 (1998)).

The data presented in the present invention demonstrate that Protac-1 can recruit MetAP-2 to SCF$^{\beta\text{-}TRCP}$ for ubiquitination. In addition, the data presented in the present invention demonstrate that Protac-1 specifies degradation of MetAP-2 by the endogenous ubiquitin/proteasome pathway in *Xenopus* egg extracts.

As one embodiment of the present invention, SCF$^{\beta\text{-}TRCP}$ was chosen as a candidate ubiquitin ligase for the development of Protac technology for two reasons. First, the apparent constitutive activity of SCF complexes (See Deshaies, R. J., *Annu. Rev. Cell Dev. Biol.*, 15:435–67 (1999)) enables a general strategy to manipulate normal or diseased cells. Second, the mechanism underlying substrate selection is well understood for SCF$^{\beta\text{-}TRCP}$. Pioneering work by Ben-Neriah and coworkers (See Yaron, A., et al., *Nature* (*London*), 396:590–94 (1998); and Yaron, A., et al., *EMBO J.*, 16:6486–94 (1997)) demonstrated that a 10-aa internal phosphopeptide mediates ubiquitination and degradation of IkBalpha. Subsequently, it was established that β-TRCP is the receptor that links this phosphopeptide to the ubiquitin/proteasome pathway (See Yaron, A., et al., *Nature* (*London*), 396:590–94 (1998); and Karin, M., et al., *Annu. Rev. Immunol*, 18: 621–63 (2000)). Furthermore, the experimental data provided by Zhou, Howley, and colleagues (See Zhou, P., et al., *Mol. Cell*, 6:751–56 (2000)) support our discovery. Zhou et al have demonstrated that engineered SCF complexes can be used to target heterologous proteins for destruction. Specifically Zhou et al. fused the human papillomavirus E7 protein to the F-box proteins Cdc4 and b-TRCP to create chimeras, which assemble to form hybrid SCF Cdc4-E7 and SCF$^{\beta\text{-}TRCP}$-E7 complexes. E7 binds tightly to retinoblastoma protein (Rb), and the F-box protein/E7 chimeras stimulate turnover of Rb by means of the SCF pathway in both yeast and mammalian cells. The F-box fusion approach depends on gene transfer of the chimeric F-box protein.

Protacs are useful research tools for manipulating the phenotype of cells by means of the targeted elimination of specific proteins, or as useful therapeutic agents for targeting the elimination of disease-promoting proteins. Furthermore, Protacs may be modified to enhance delivery to cells. For example, attachment of the tat peptide (See Nagahara, H., et al., *Nat. Med.*, 4:1449–52 (1998)) may promote transduction of Protac-1 into cells, or a β-TRCP-binding peptide that is derived from the HIV Vpu protein (See Margottin, F., et al., *Mol. Cell.*, 1:565–74 (1998); and Schubert, U., et al., *J. Virol.*, 72:2280–88 (1998)), and that is phosphorylated by constitutively active casein kinase II may allow delivery of an unphosphorylated Protac to cells. Alternatively one could identify small molecules that can substitute for the E3 targeting activity of the IPP.

Figure 6:
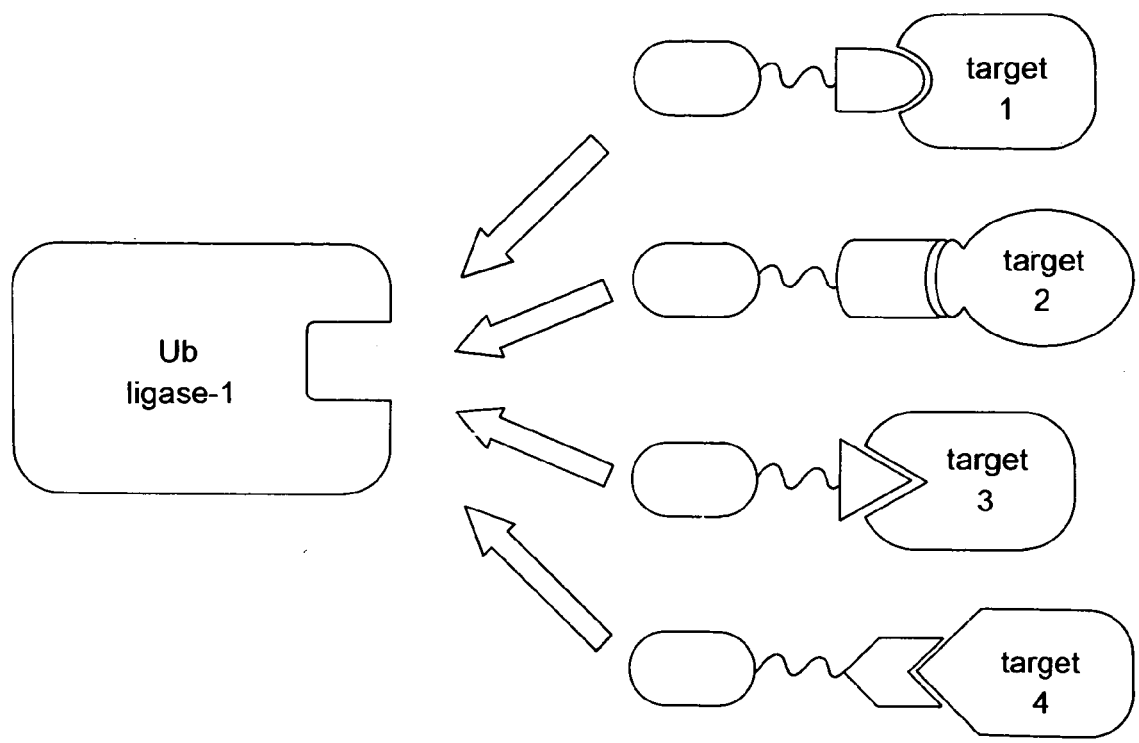
FIG. 6 depicts the general schematic of how different disease-promoting proteins might be recruited to different ubiquitin ligases for ubiquitination and degradation by unique Protacs.
Figure 6:
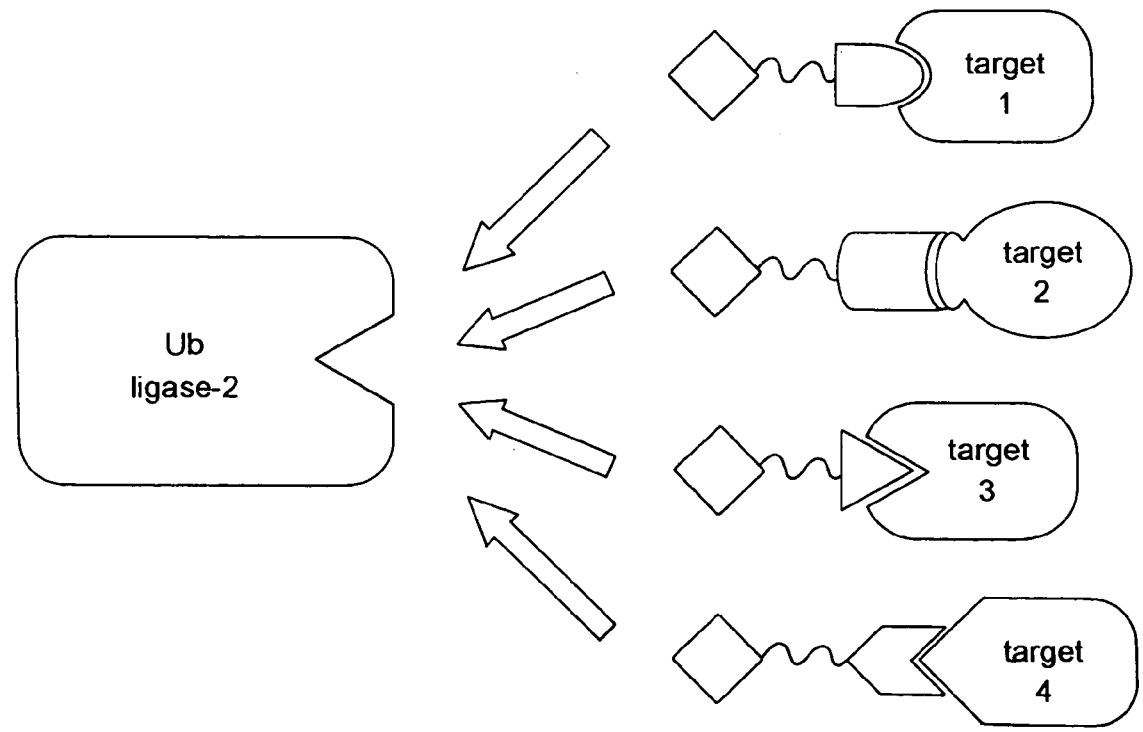

The present invention also provides methods to develop an entire suite of Protac compounds (FIG. 6). Several approaches have been developed for identifying small molecules that bind to any target protein of interest (See Borchardt, A., et al., *Chem. Biol*, 4:961–68(1997); MacBeath, G., et al., *J. Am. Chem. Soc.*, 121:7967–68 (1999); and You, A. J., et al., *Chem. Biol.*, 4:969–75 (1997)). Candidates emerging from such screens would serve as platforms for the production of new Protacs, regardless of the topology of their interaction with the target protein. Because the human genome encodes a large number of RING-and HECT-based ubiquitin ligases, the present invention could be used to develop multiple Protacs that target a single protein to allow for fine-tuning its rate of degradation. Moreover, because some ubiquitin ligases are likely to exhibit restricted patterns of expression, the present invention can be used to develop Protac-based drugs whose effects are limited to specific tissues.

Although the invention has been described with reference to the presently preferred embodiment, it should be understood that various modifications can be made without departing from the spirit of the invention. Accordingly, the invention is limited only by the following claims.

What is claimed is:

1. A composition comprising:
   a) a ubiquitin pathway protein binding moiety, wherein the ubiquitin pathway binding moiety is IkB-alpha or an IkB-alpha peptide; and
   b) a target protein binding moiety covalently coupled to the ubiquitin pathway protein moiety of a), wherein the target protein binding moiety is ovalicin.

2. The composition according to claim 1, wherein the composition binds methionine amino-peptidase 2 (MetAP 2).

3. The composition of claim 1, wherein the ubiquitin pathway binding moiety is an IkB-alpha peptide.

4. The composition of claim 3, wherein the IkB-alpha peptide is as set forth in SEQ ID NO: 1.

* * * * *

UNITED STATES PATENT AND TRADEMARK OFFICE
CERTIFICATE OF CORRECTION

| | | |
|---|---|---|
| PATENT NO. | : 7,041,298 B2 | |
| APPLICATION NO. | : 09/953473 | |
| DATED | : May 9, 2006 | |
| INVENTOR(S) | : Deshaies et al. | |

It is certified that error appears in the above-identified patent and that said Letters Patent is hereby corrected as shown below:

In the Specification

COLUMN 1, LINE 11

Please insert the following title and paragraph beginning on Line 11 of Column 1 prior to the paragraph entitled "FIELD OF THE INVENTION", specifically:

--GRANT INFORMATION

This invention was made with government support under GM062120 awarded by National Institutes of Health. The government has certain rights in the invention.--

Signed and Sealed this
Twenty-seventh Day of May, 2014

Michelle K. Lee
*Deputy Director of the United States Patent and Trademark Office*